United States Patent
Dilhaire et al.

(10) Patent No.: US 7,728,317 B2
(45) Date of Patent: Jun. 1, 2010

(54) OPTICAL HETERODYNE SAMPLING DEVICE HAVING PROBE AND PUMP BEAMS

(75) Inventors: Stefan Dilhaire, Talence (FR); Wilfrid Claeys, Talence (FR); Jean-Michel Rampnoux, Pessac (FR); Clément Rossignol, Bordeaux (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 0 days.

(21) Appl. No.: 12/090,893

(22) PCT Filed: Oct. 20, 2006

(86) PCT No.: PCT/FR2006/002384

§ 371 (c)(1),
(2), (4) Date: Apr. 21, 2008

(87) PCT Pub. No.: WO2007/045773

PCT Pub. Date: Apr. 26, 2007

(65) Prior Publication Data

US 2008/0251740 A1 Oct. 16, 2008

(30) Foreign Application Priority Data

Oct. 21, 2005 (FR) .................................. 05 10776

(51) Int. Cl.
*H01J 40/14* (2006.01)
(52) U.S. Cl. ............... 250/578.1; 250/458.1; 356/237.1
(58) Field of Classification Search ............. 250/578.1, 250/458.1, 461.1, 461.2; 356/237.1
See application file for complete search history.

(56) References Cited

U.S. PATENT DOCUMENTS

| 5,778,016 A | 7/1998 | Sucha et al. |
| 5,814,820 A * | 9/1998 | Dong et al. ............... 250/458.1 |
| 2004/0196453 A1* | 10/2004 | Some ..................... 356/237.1 |

OTHER PUBLICATIONS

Rossignol et al., "Nondestructive evaluation of micrometric diamond films with an interferometric picosecond ultrasonics technique," J. of Appl Phys., vol. 95, No. 8, pp. 4157-4162 (Apr. 15, 2004).
Cote et al., "Refractive index, sound velocity and thickness of thin transparent films from multiple angles picosecond ultrasonics," Rev. of Sci. Inst., vol. 76, No. 5, pp. 53906-1-53906-6 (Apr. 29, 2005).
Spence et al., "Time synchronisation measurements between two self-modelocked Ti:sapphire lasers," Optics Comm., vol. 101, No. 3/4, pp. 286-296 (Aug. 15, 1993).

* cited by examiner

*Primary Examiner*—Seung C Sohn
(74) *Attorney, Agent, or Firm*—Young & Thompson (57) ABSTRACT

An optical heterodyne sampling device includes: two pulsed laser sources which may have a jitter and which can receive respectively a pump beam and a probe beam having respective repetition frequencies Fs and Fp, whereby Fs≠Fp; and an element for combining the pump beam and the probe beam which are intended to be passed over a sample, consisting of a signal channel including a system for the photodetection of the response signal from the sample and a system for acquiring the photodetected signal, which is connected to the signal channel. According to the invention, Fs and Fp are essentially constant and the acquisition system includes an acquisition trigger element. A synchronization channel is connected to the trigger element, and includes a device for measuring the beat frequency |Fs−Fp| which can generate a synchronization signal comprising pulses each time the pulses of the pump beam and the probe beam coincide.

33 Claims, 10 Drawing Sheets

OPTICAL HETERODYNE SAMPLING DEVICE HAVING PROBE AND PUMP BEAMS

BACKGROUND OF THE INVENTION

1. Field of the Invention

The field of the invention is the ultra high-speed, non-destructive measurement of the mechanical, thermal or optical properties of a material. Ultra High-speed measurement is understood to mean a measurement with a temporal resolution of the order of a picosecond.

2. Description of the Related Art

It is known to obtain measurements with a temporal resolution of this type via optical sampling techniques using two pulse trains respectively designated "pump" and "probe" trains, with pulse period T, each pulse having a duration τ of approximately 100 femtoseconds.

The pump beam causes a disturbance in the material or sample which in response produces an optical signal dependent on the optical properties thereof (reflectivity, absorption, expansion, contraction etc.). The probe beam is delayed by a quantity $T_{ps}$ referred to as the "pump-probe" delay and reads the reaction of the material; it is generally of a low intensity relative to that of the pump beam. The temporal reaction of the material is reconstructed by varying this delay between zero and a duration equal at most to the period T of the pulse train. In practice, this duration is much less than T. Typically T is of the order of 13 ns and the variation in the delay is then typically limited to 2 or 3 ns.

Figure 1:
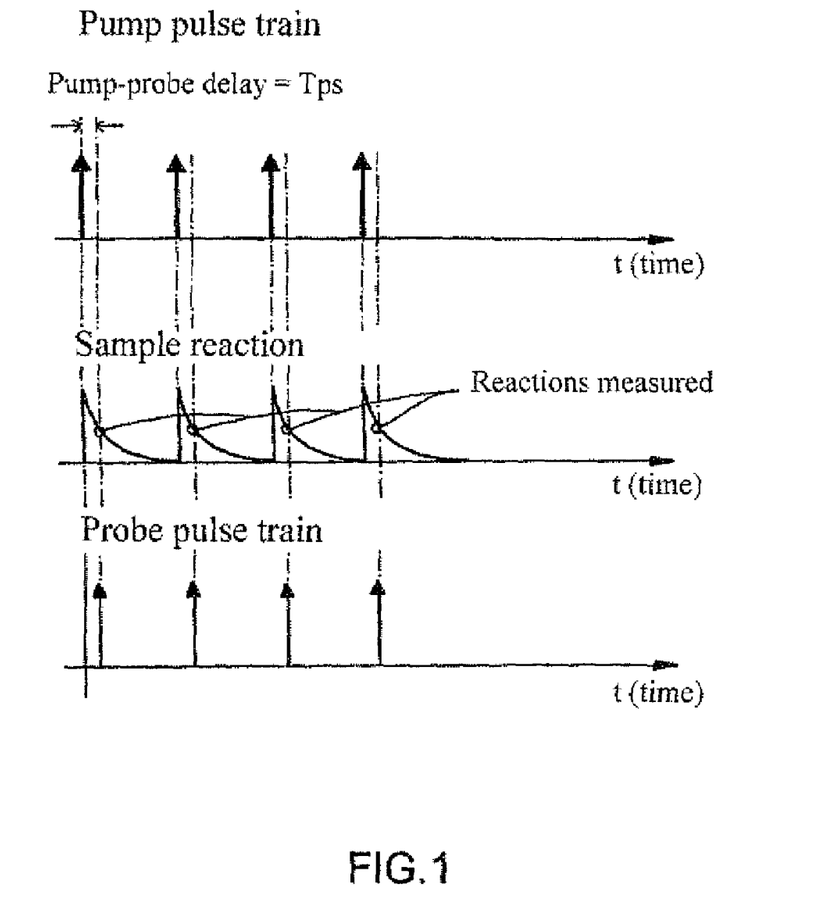
FIG. 1 schematically shows pump and probe pulse trains and the reaction from a sample, as a function of time, in the case of homodyne sampling, FIG. 2 as described above schematically shows a homodyne sampling device according to the state of the art.
Figure 2:
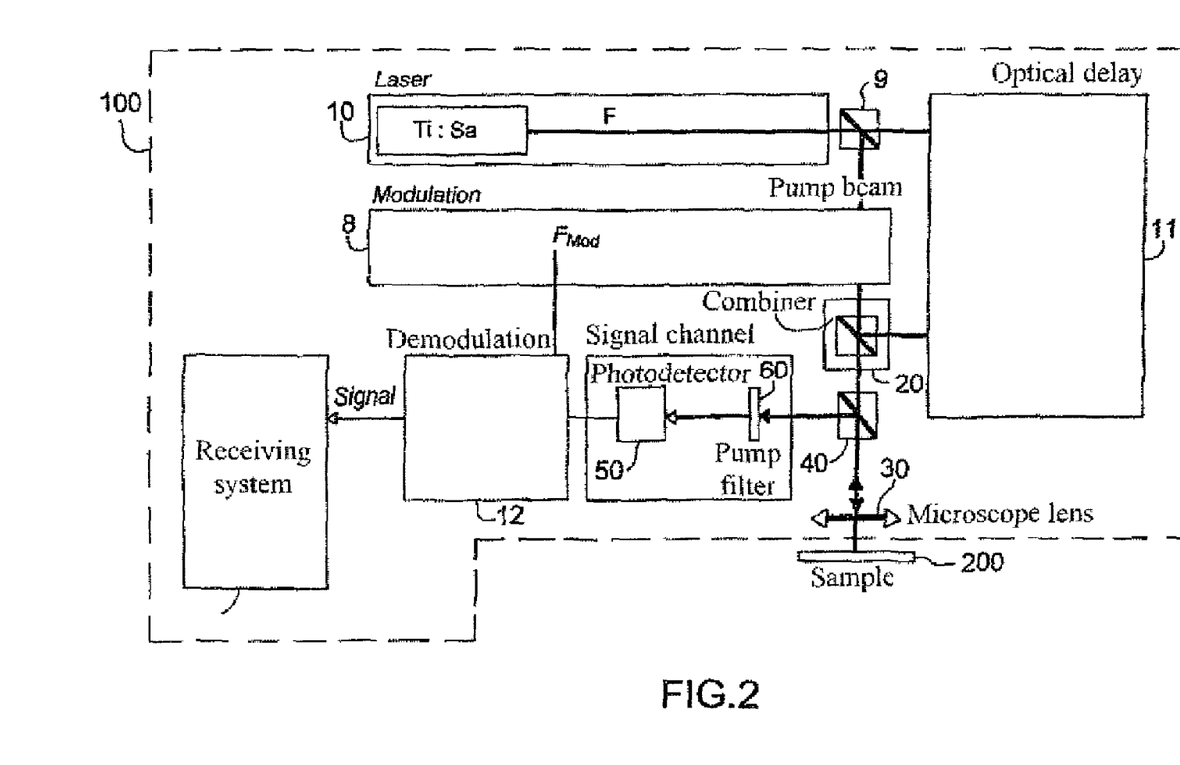

Usually, both the pump and the probe pulse train have the same pulse repetition period T and the sampling is thus termed "homodyne". FIG. 1 shows, in the case of homodyne sampling, pump and probe pulse trains offset by a delay $T_{ps}$ along with the value of the sample reaction obtained for this delay. An example of an assembly allowing this technique to be made use of is schematically shown in FIG. 2. The homodyne sampling device 100 comprises a laser source 10 connected to a splitter 9 which can split the laser beam into a pump beam, modulated by a modulator 8, and a second, probe beam which is delayed by an optical delay line 11. The purpose of the modulator is to convert the signal to have a higher frequency in order to disengage said signal from the noise in the range of 1/f, f being the frequency of the signal. The two beams are subsequently combined by a combiner 20 before being focussed to appoint onto the sample 200 via a microscope lens 30. In the example in the figure, the sample reaction is obtained by reflection. The reaction is directed to a photodetector 50 after being filtered by a pump beam filter 60. The photodetector is connected to an acquisition system 70, via a demodulator 12 which allows the signal to be re-established in the baseband.

The delay $T_{ps}$ is produced and controlled by an optical delay line comprising a mechanical translation system of a mirror disposed in the path of one of the beams. The delay is related to the translation by the formula:

$$T_{ps}=d/c$$

where d is the length of the delay line and c is the speed of light.

Bearing in mind the orders of magnitude, a length d of 30 μm causes a delay of 100 fs. In practice, the length of the delay line is limited. In fact, a displacement of more than 30 cm significantly affects the focussing to a point of one beam relative to the other. A delay of 10 ns, which requires a length d of 3 m, is thus very difficult to achieve. A limit of 2 to 3 ns on the temporal delay corresponds to this limit on the displacement: the temporal reaction of the material is reconstructed only over approximately 2 to 3 ns.

Moreover, these displacements are achieved with a negative effect on the stability of the focussing to a point of the laser beam onto the sample.

Further, the vibrations brought about by the displacement of the delay line deteriorate the signal to noise ratio and considerably increase the measurement time. It usually takes 30 to 40 minutes to obtain a signal over several nanoseconds, i.e. to effect the different displacements so as to scan the reaction of the material over times of up to $T_p$ or approximately 13 ns.

SUMMARY OF THE INVENTION

Figure 3:
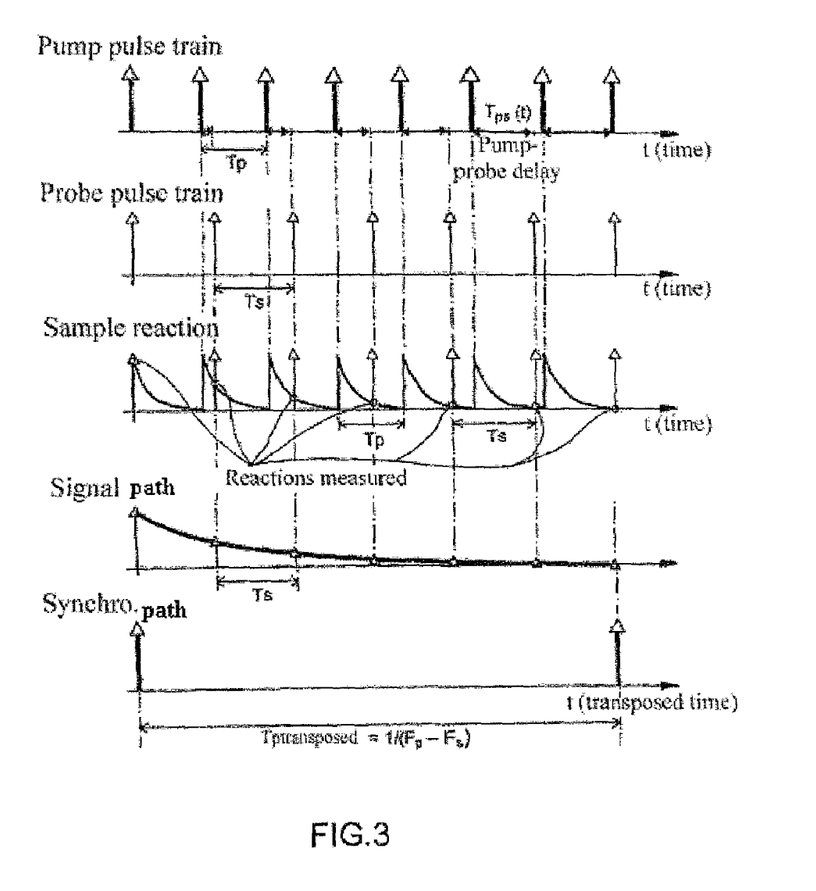
FIG. 3 schematically shows pump and probe pulse trains and the reaction from a sample, as a function of time, in the case of heterodyne sampling, FIG. 4 as described above schematically shows an exemplary heterodyne device according to the invention, FIG. 5 schematically shows an exemplary representation of the pulse reaction of a tungsten film, as a function of time, as obtained with a device according to the invention, FIGS. 6a, 7a, 8a, 9a, 10a schematically show examples of heterodyne sampling devices according to the invention, equipped with a scanning device, and FIGS. 6b, 7b, 8b, 9b, 10b schematically show the paths of the pump and probe beams through the corresponding scanning devices and the lens up as far as the sample.

In order to overcome these difficulties, one solution involves using a pump beam with pulse period repetition $T_p$ and a probe beam with period $T_s$ where $T_p$ is different from $T_s$. This sampling is thus termed "heterodyne". FIG. 3 shows, in the case of heterodyne sampling, pump and probe pulse trains offset by a delay $T_{ps}$ along with the value of the sample reaction obtained for this delay. The delay $T_{ps}$ between the pump and probe pulse trains is no longer fixed, as in the case of homodyne sampling, but changes over time. Whilst $T_p-T_s$ is fixed, the delay $T_{ps}$ varies linearly between 0 and $T_p$. The period $T_p$ is scanned in a time equal to $1/\Delta F$ where $\Delta F=|F_s-F_p|$, $\Delta F$ being termed the beat frequency, $F_p$ is equal to $1/T_p$ and is the repetition frequency of the pump beam, and $F_s$ is equal to $1/T_s$ and is the repetition frequency of the probe beam.

This technique allows the sample reaction to be measured without mechanical translation and thus without alteration of the beam focus point on the sample.

The delay $T_p-T_s$ does not actually vary linearly, as the frequencies $F_p$ and $F_s$ vary at random because of the natural jitter of the lasers. This jitter has the effect of randomly modulating the beat frequency ΔF by a quantity g(t). This phenomenon is even more significant if it is desired that a reduced temporal resolution be obtained. In fact, for a period $T_p$ of 13 ns, 13,000 measurements are required to achieve a temporal resolution of 1 ps, since the uncertainty introduced by the jitter for each measurement accumulates over time. The jitter thus has the effect of limiting the temporal resolution.

The object of the invention is to allow measurements with a temporal resolution of approximately 1 ps or less (100 fs) to be obtained, without the need to carry out mechanical translation and without being disadvantaged either by a very long acquisition time or by the jitter.

More specifically, the invention relates to an optical heterodyne sampling device comprising two pulsed laser sources, which are configured to emit respectively a pump beam and a probe beam having respective repetition frequencies $F_s$ and $F_p$ where $F_s \neq F_p$, and an element for combining the pump and probe beams which are to be directed onto a sample, and further comprising a signal path, comprising a photodetection system of the sample reaction signal, and a system for acquiring the reaction signal which is connected to said signal path. The device is principally characterised in that, $F_s$ and $F_p$ being substantially constant and the acquisition system comprising an acquisition triggering element, the device comprises a synchronisation path, which is connected to said triggering element and having a device for measuring the beat frequency $|F_s-F_p|$ adapted to generate a synchronisation signal including pulses for each time the pump and probe beam pulses coincide.

This synchronisation channel allows the acquisition system to locate the initial instant of the reaction, i.e. the instant when the pump pulses coincide with the probe pulses on the sample. This allows the effect of the natural jitter of the lasers on the temporal resolution to be minimised.

According to one feature of the inventions the measuring device comprises a two-photon photodiode.

According to a further feature of the invention, said device comprises a device for coupling one laser source to the other, having for example a frequency divider which is disposed at the output of one laser source and a frequency synthesiser which is connected to said divider and to the other laser source.

The photodetection system may be a photodetector or a row of photodetectors or a grid of photodetectors.

The laser sources may optionally have the same wavelength.

The pulse frequencies $F_p$ and $F_s$ are preferably between 1 kHz and 10 GHz, more specifically between 1 kHz and 100 MHz.

According to one feature of the invention, the synchronisation path having the device for measuring $|F_s-F_p|$ is disposed in the path of the sample reaction signal. In this case, the device according to the invention comprises a sample reaction signal separator, in two paths, the signal path being disposed on one path and the synchronisation path on the other path.

According to a further feature of the invention, the synchronisation path is disposed in the path of the pump and probe beams which are to be directed onto the sample.

The device according to the invention preferably comprises, disposed at the input of the photodetection system, a filter for the pump beam coming from the sample, along with a low-pass filter disposed at the output of the reaction signal photodetection system.

It is advantageous for the beat frequency $|F_s-F_p|$ to be between 1 Hz and 100 kHz.

According to one feature of the invention, the laser sources emit pulses having a duration of between 10 fs and 10 picoseconds.

It is advantageous for the temporal resolution to be approximately equal to one picosecond. According to one embodiment of the invention, the device comprises a device for scanning the pump beam and/or the probe beam onto the sample.

According to one feature of the invention, the scanning device comprises two lenses and an element for displacing the beam or beams, which may be a translation plate of a lens or may comprise two galvanometric mirrors which can pivot respectively around two perpendicular axes.

According to a further feature of the invention, the scanning device is adapted to displace the pump beam and the probe beam, and the combiner comprises said scanning device.

According to a further feature of the invention, the scanning device can displace the pump beam and the probe beam and is disposed downstream from the combiner.

The scanning device may comprise a plate for translating the sample.

The invention further relates to method for optical heterodyne sampling, using a device comprising two laser sources, which emits respectively a pump pulse beam and a probe pulse beam having respective repetition frequencies $F_s$ and $F_p$ where $F_s \neq F_p$, including a step of combining the pump and probe beams, a step of directing the combined pump and probe beams onto a source, a step of photodetecting the sample reaction, and a step of acquiring the detected photosignal, characterised in that, $F_s$ and $F_p$ being substantially constant, the method further includes a step of measuring the beat frequency $|F_s-F_p|$ in order to isolate an instant of coincidence between the pump and probe pulses, and in that the acquisition step is triggered as a function of the instant of coincidence.

According to one feature of the invention, the method further comprises a step of coupling one laser source to the other.

The beat frequency $|F_s-F_p|$ is preferably substantially equal to $\tau F_s F_p$, where $\tau$ is the duration of the probe beam pulses.

According to one feature of the invention, the sample reaction is obtained by reflection or transmission of the pump and probe beams.

According to a further feature of the invention, the method comprises a step of scanning the pump and/or probe beams onto the sample.

The pump and probe beams can be superimposed.

The sample may be a material in thin layers, an integrated circuit a semiconductor, a biological cell or a chemical reagent.

It is advantageous for the sampling to have a temporal resolution of the order of a picosecond.

According to one feature of the invention, the laser sources emit pulses having a duration of approximately 100 femtoseconds.

The beat frequency $|F_s-F_p|$ is preferably between 1 Hz and 100 kHz.

The pulse frequencies $F_s$ and $F_p$ may for example be between 1 kHz and 100 MHz.

BRIEF DESCRIPTION OF THE DRAWINGS

Further features and advantages of the invention will be apparent from the following detailed description, given by way of non-limiting example and with reference to the appended drawings, in which.

DETAILED DESCRIPTION OF THE INVENTION

The same components are given the same references in each figure.

The invention is based on the principle of heterodyne sampling, which allows the carrying out of a mechanical translation to be avoided and allows the acquisition time to be reduced considerably. The device 150 according to the invention, described in relation to FIG. 4, thus comprises in the conventional manner a pump pulse laser source 10 and a probe pulse laser source 15, which can respectively emit a pump beam and a probe beam. The duration of the pulses of the pump beam is generally not equal to that of the pulses of the probe beam, but they may be equal. In the following, the pulse duration τ under consideration is that of the probe beam pulses. The pump and probe beams do not generally have the same wavelengths, but they may be equal.

Figure 4:
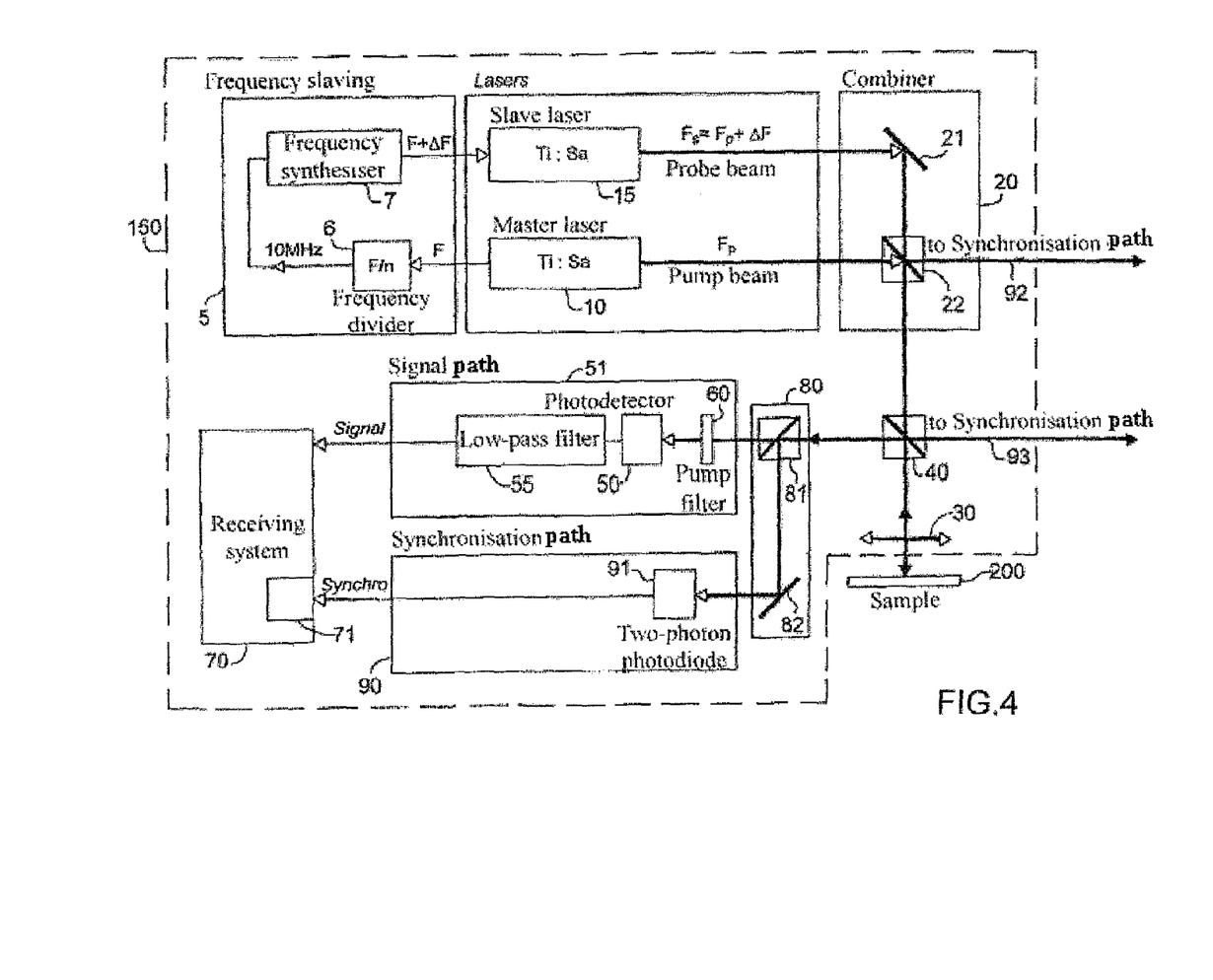

The beams are combined by a combiner 20, which comprises for example a mirror 21 and a semi-transparent slide 22, before being directed onto the sample 200 which is to be measured, via a focussing element 30 such as a lens. The sample reaction, which is obtained by reflection as is shown in the figure or by transmission, is received by a photodetector 50 then transmitted to an acquisition system 70. A pump filter 60 is preferably disposed before the photodetector 50 to filter the residual pump signal. A low-pass filter 55 is advantageously disposed between the photodetector 50 and the acquisition system 70 to eliminate the laser pulses superimposed on the reaction. Signal path 51 represents these 3 components 60, 50 and 55 as a whole.

The jitter has the effect of limiting the temporal resolution $T_p - T_s$. Thus, in fact:

$$T_p - T_s = \Delta F / F_p F_s$$

As the temporal resolution is equal to $\Delta F/F_p F_s$ (or $\Delta F/F_s^2$ when $\Delta F$ is small relative to the laser frequency), the modulation of $\Delta F$ limits the temporal resolution.

One solution for minimising the effect of the natural jitter of the lasers on the temporal resolution consists of isolating the initial instant of the reaction, i.e. the instant when the pump pulses coincide with the probe pulses on the sample, as shown in FIG. 3 by the graph "Synchronisation path". This involves reconstructing the time scale of the sample reaction in transposed time.

The device 150 according to the invention thus comprises, in addition to the signal path, a synchronisation path 90 which comprises a measuring device 91 for measuring $|F_s - F_p|$ which can produce a synchronisation signal consisting of pulses for each time the pump and probe laser pulses coincide on the sample. Said synchronisation signal is proportional to the product of the pump pulse train or signal and the probe pulse train or signal. The measuring device 91 comprises for example a two-photon photodiode. The measurement is carried out from a reaction signal, part of which is retrieved before the signal path by a divider 80 which includes for example a semi-transparent slide 81 and a mirror 82.

According to a variant this synchronisation channel 90 is disposed before the sample 200: the measurement is then carried out by retrieving part of the pump and probe beams before the sample. This variant is designated by reference numeral 92 or 93.

The acquisition system 70 comprises a triggering element 71 for triggering the acquisition. The synchronisation path 90 (or 92 or 93) is connected at the output thereof to this element 71, which may then trigger the reception of the reaction at the instant of coincidence. This instant is the initial instant also referred to as time zero.

The effect of the jitter may be even further reduced in the following manner. Within a first time, the effect of the jitter on the delay $T_{ps}$ is calculated.

Let:

$1_p(2\pi F_p t)$ be the pump pulse train and $1_p(2\pi F_p(t-T_{ps}(t)))=1_p((2\pi F_s t)$ be the probe pulse train.

The instantaneous frequency of the probe pulse train is written as:

$$F_s(t) = \frac{dF_p(t - T_{ps}(t))}{dt} = F_p\left(1 - \frac{dT_{ps}(t)}{dt}\right)$$

A linear variation in the delay is obtained if the frequency of the probe pulse train is offset by a fixed amount:

$$|F_s - F_p| = \Delta F = F_p \frac{dT_{ps}(t)}{dt}$$

Thus, the delays vary from zero to $T_p$ (discretely, according to the temporal resolution). The period of the pulse trains is scanned in a time equal to the reciprocal of the beat frequency $\Delta F$. The sample reaction is observed in a transposed time scale in which $\Delta T_{ps}/\Delta t = \Delta F/F_p$. This dilation of the time scale allows the spectrum of the reaction signal to be transposed within the bandwidth of the detector.

The variation of $T_{ps}$ actually contains a noise term: the jitter $g(t)$, which is the random frequency variation. The jitter has the effect of randomly modulating the beat frequency by an amount $g(t)$.

Thus:

$$\frac{dT_{ps}(t)}{dt} = \frac{\Delta F + g(t)}{F_p}$$

$$T_{ps}(t) + \Delta T_{ps} = \int_0^t \frac{\Delta F}{F_p} du + \frac{1}{F_p} \int_0^t g(u) du$$
$$= \frac{\Delta F}{F_p} t + \frac{1}{F_p} \int_0^t g(u) du$$

The uncertainty $\Delta T_s$ is amplified over time:

$$|\Delta T_{ps}| = \frac{1}{F_p}\left|\int_0^t g(u) du\right| = \frac{1}{F_p}\langle g \rangle \cdot t$$

Over a measurement period, this uncertainty is:

$$|\Delta T_{ps}| = \frac{1}{F_p}|\langle g \rangle| \cdot T_{transpose} = \frac{1}{F_p}|\langle g \rangle| \cdot \frac{1}{\Delta F} = T_p |\langle g \rangle| \cdot \frac{1}{\Delta F}$$

To minimise this uncertainty, the jitter must be negligible compared to the beat: the beat $\Delta F$ is selected to be substantial. Said beat is limited, however: the upper bound for $\Delta F$, designated $\Delta F_{max}$, is imposed by the temporal resolution which it is desired to achieve.

The resolution is inherently limited by the duration τ of the pulses: $\tau \geq |\Delta F|/|T_s - T_p|$ Thus: $\tau \geq |\Delta F|/(F_s \cdot F_p)$ Hence: $\Delta F_{max} = \tau F_p F_s$ For lasers Sa: Ti with pulse frequencies $F_p$ and $F_s$ of 76 MHz delivering 100 fs pulses (τ=100 fs), a beat $\Delta F_{max}$ of 600 Hz is obtained for a maximum temporal resolution equal to 100 fs. The jitter must thus be much less than a few Hz for the resolution to be obtained.

To minimise the effect of the jitter, the frequency of one of the two pulse trains may therefore be coupled to that of the other pulse train, using a coupling device 5 shown in FIG. 4. This device may for example be a device for controlling the length of one of the two laser cavities. The synchronisation input of a frequency synthesiser 7 is used in that a reference signal F/n is inputted there by a frequency divider 6 of the pulse train of one of the two laser sources 10, which takes the master role. The output of the frequency synthesiser 7 is subsequently offset by the amount ΔF and the signal F+ΔF is used as a command by the control system of the slave laser source 15.

The master laser source is the pump laser source and the slave laser source is the probe laser source as shown in the figure. The reverse is also possible, with the probe laser source as the master laser source and the pump laser source as the slave laser source.

When the frequencies of the two, pump and pulse laser sources are coupled, the beat may be as weak as the performance of the device allows (typically some fraction of a Hertz).

Once the effect of the jitter has been minimised, the maximum resolution as limited by the pulse duration τ may be achieved if $\Delta F \leq \tau F_s F_p$.

The bandwidth of the low-pass filter currently under consideration is defined as follows: the reaction time of the low-pass filter is equal to the reciprocal of the bandwidth thereof.

$\tau_R \approx 1/B_d$.

The desired temporal resolution $\tau_{eff}$ becomes, in transposed time, the reaction time $\tau_R$ of the low-pass filter.

Given that $\tau_{eff} = \tau_R \Delta F / F_p$, it may be deduced that $\tau_{eff} \approx \Delta F / B_d F_p$.

With ΔF=600 Hz and $F_p$=76 MHz, a bandwidth of 8 MHz is obtained for an effective temporal resolution of 1 ps.

The following table summarises the features and performances of the tests carried out.

|  | Denoted | Values | Units |
| --- | --- | --- | --- |
| Pump frequency | $F_p$ | 76 | MHz |
| Probe frequency | $F_s = F_p + \Delta F$ | 76.0006 | MHz |
| Beat | ΔF | 600 | Hz |
| Temporal window | $1/F_p$ | 13 | ns |
| Transposed temporal window | $T_{tr} = 1/\Delta F$ | 1.66 | ms |
| Measurements per period | $N = F_s/\Delta F$ | 126,666 | units |
| Maximum resolution | $\Delta F/F_s F_p$ | 100 | fs |
| Pulse duration | τ | 100 | fs |
| Low-pass filter bandwidth | $B_d = 1/\tau_R$ | 8 | MHz |
| Effective temporal resolution | $\tau_{eff} = \Delta F/B_d F_p$ | 1 | ps |

Figure 5:
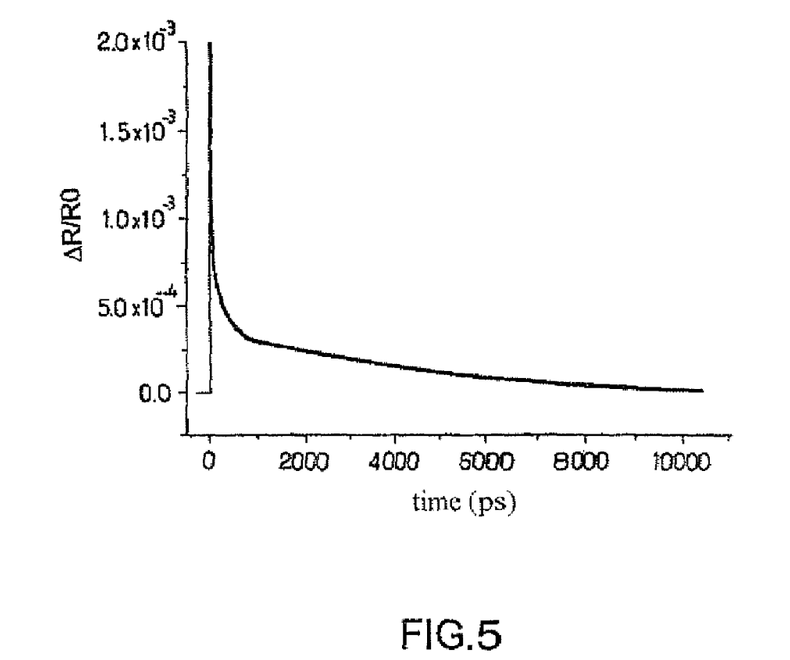

FIG. 5 shows a graph of the pulse reaction to the reflectivity R obtained on a tungsten film 280 mm thick over a duration $T_p$ of 13 ns with a heterodyne sampling device according to the invention. More precisely, the measurement is of the pulse reaction to ΔR/R0, R0 being the average reflectivity of the tungsten film and ΔR the variation in the reflectivity. There is a one picosecond temporal resolution, the time range being extended up to the period $T_p$ of the pulse train of the order of 13 ns, and the acquisition time of 30 seconds thus being divided by a factor of 10 to 50, by comparison with a homodyne sampling device for a time range of about 1 ns, i.e. 10 times smaller.

The sampling method according to the invention applies in particular to the measurement of optical, thermal and mechanical properties of materials in thin layers, from a few nm to a few μm, to analysing defects in microelectronics, to picosecond acoustics, to studying the transfer of heat to small regions of space (nm-μm) over short times (fs-μs), to studying nano-objects and nano-materials, to studying chemical reactions, and to tracking biological tracers.

The sampling device according to the invention may be connected to a device for scanning the pump and/or probe beams onto the sample 200. For each position of the beam or beams on the sample, the temporal reaction signal is registered as disclosed above. The maximum temporal resolution is the duration of the laser pulses. This sampling device may thus be applied to high-speed imaging.

From the scanning of the surface of a sample, a film of the scanned surface response may be reconstructed with a resolution of the order of $10^{12}$ images per second during the time range between two pump laser pulses, i.e. 12 ns. Scanning of this type has been carried out with a tungsten film 250 nm thick, with surface area 15×15 μm², as a sample.

Figure 6A:
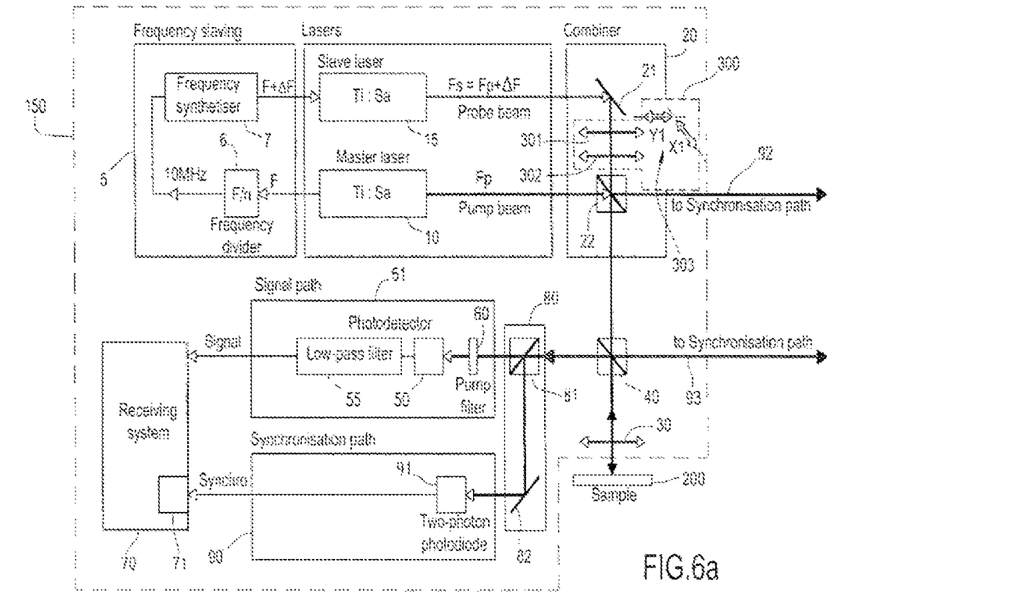
Figure 6B:
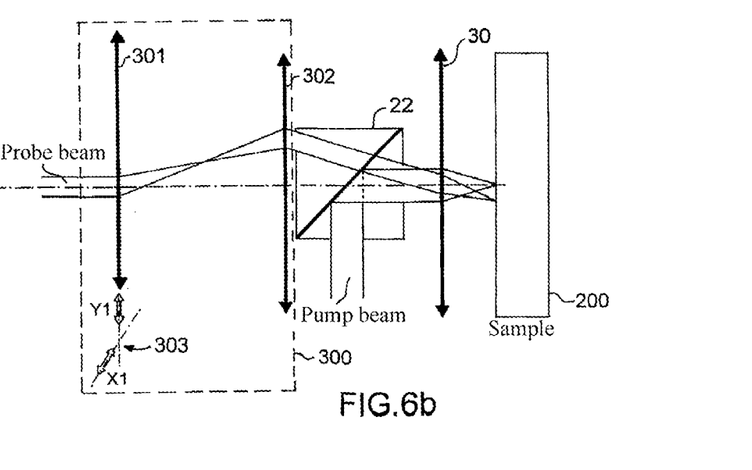
Figure 7A:
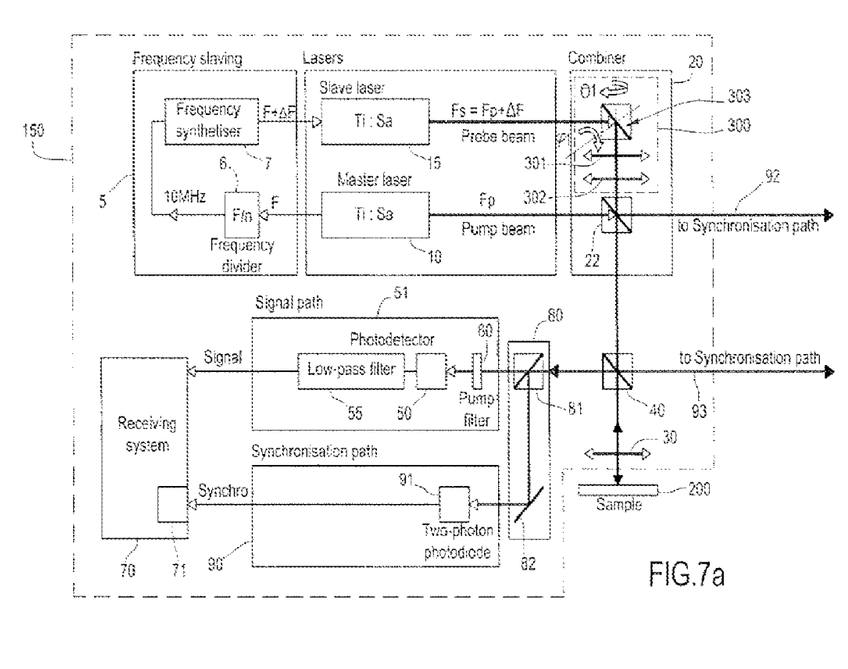
Figure 7B:
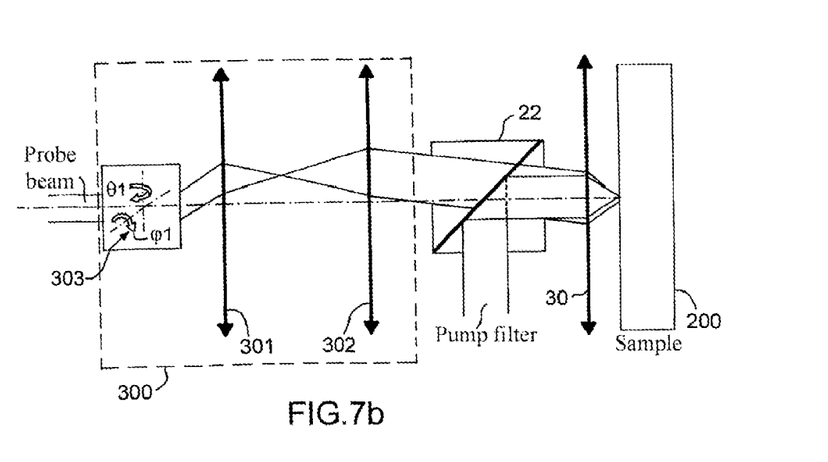
Figure 8A:
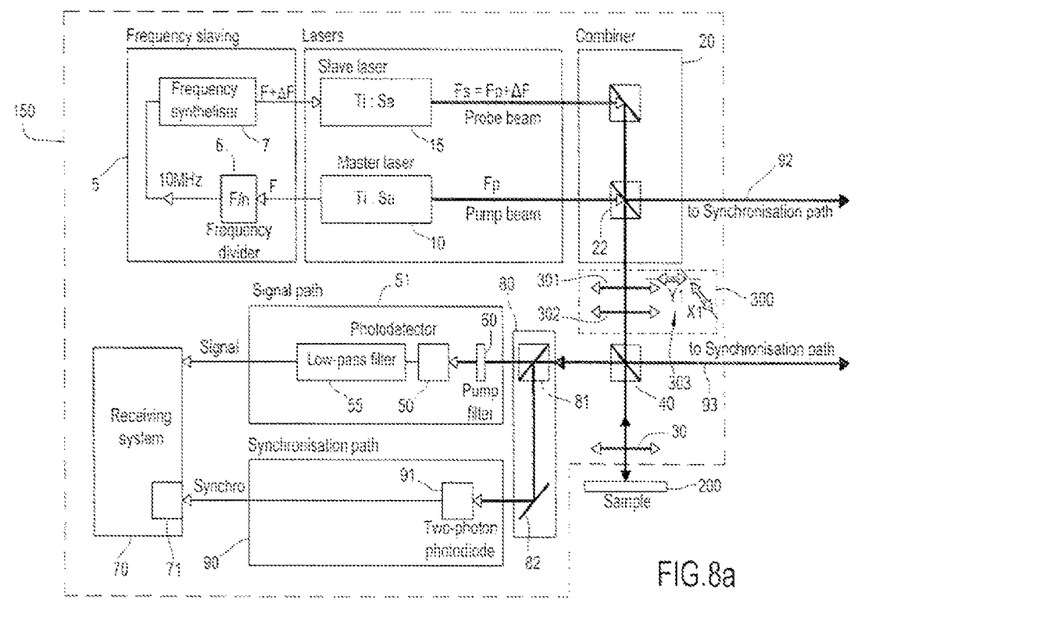
Figure 8B:
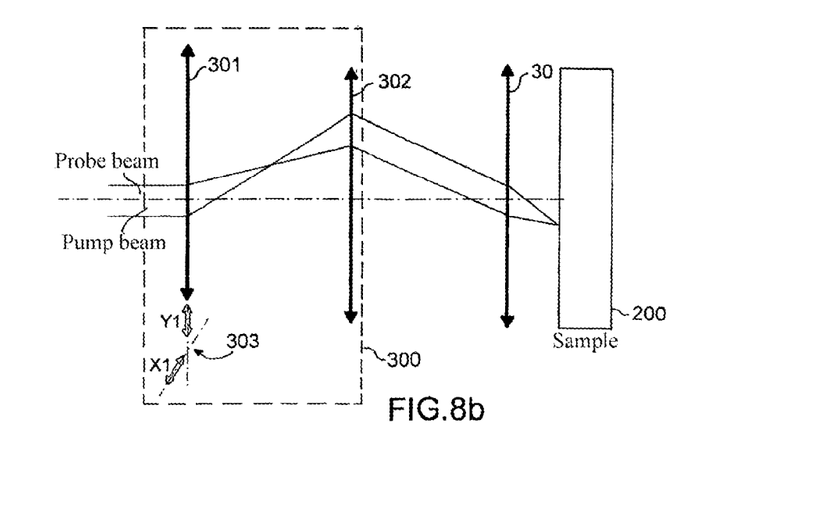
Figure 9A:
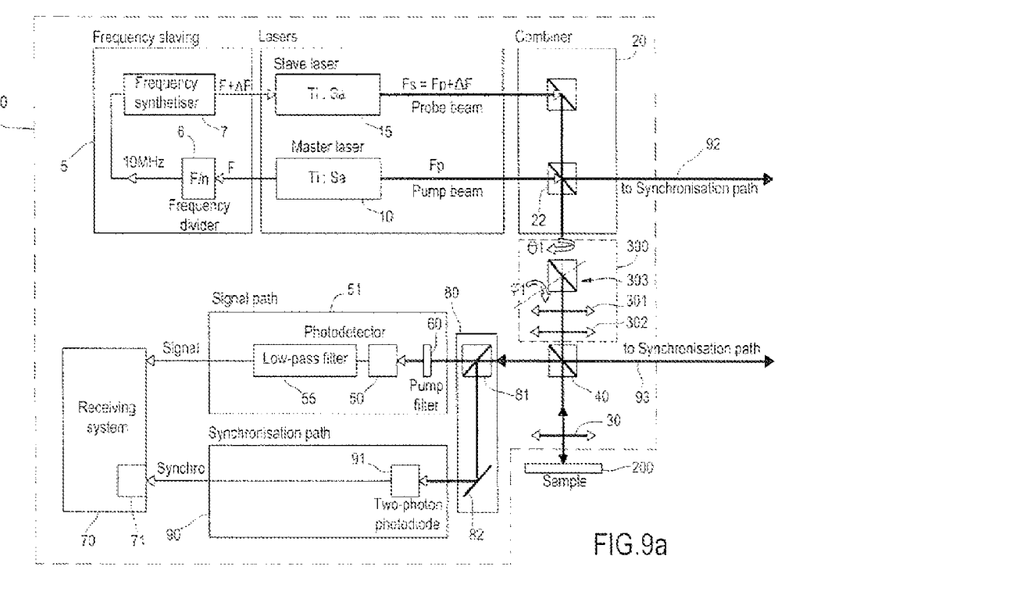
Figure 9B:
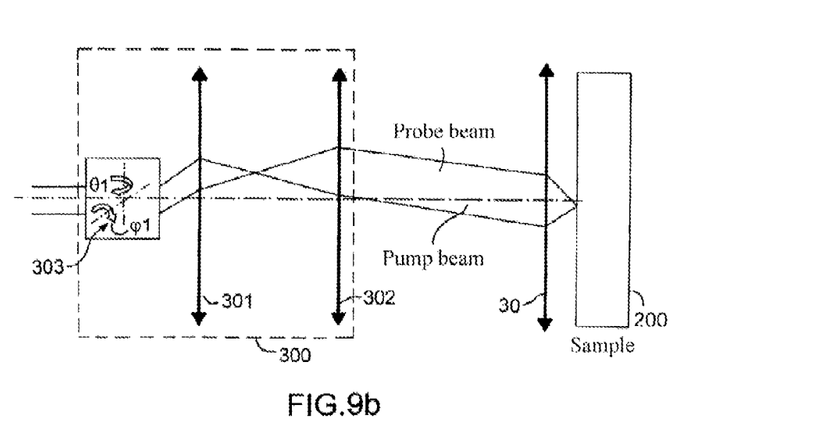

The scanning device 300 comprises two lenses 301 and 302 of focal lengths $f_1$ and $f_2$, disposed at a distance $f_1+f_2$ from one another, and an element 303 for displacing the beam or beams, as shown in FIGS. 6 to 9. This displacement element 303 is a translation plate of a lens in a plane X, Y parallel to that of the sample, as shown in FIGS. 6 and 8, or comprises two galvanometric mirrors which can pivot around their respective perpendicular axes $\phi_1$, $\theta_1$ as shown in FIGS. 7 and 9. The b figures show the paths of the pump and probe beams through the corresponding scanning device 300 and the lens 30 up to the sample 200.

According to a first embodiment, described with reference to FIGS. 6a and 7a, the scanning device 300 is included in the combiner 20, for example upstream from the semi-transparent slide 22; the beams are combined by the combiner 20 but are not superimposed. The probe beam scans the sample 200 whilst the pump beam remains in a fixed position on the sample.

According to a second embodiment, described with reference to FIGS. 8a and 9a, the scanning device 300 is downstream from the combiner 20; the pump and probe beams are combined and superimposed by the combiner 20 and are superimposed on the sample 200.

In the above embodiments, the pump and/or probe beams are displaced, the sample 200 being fixed.

Figure 10A:
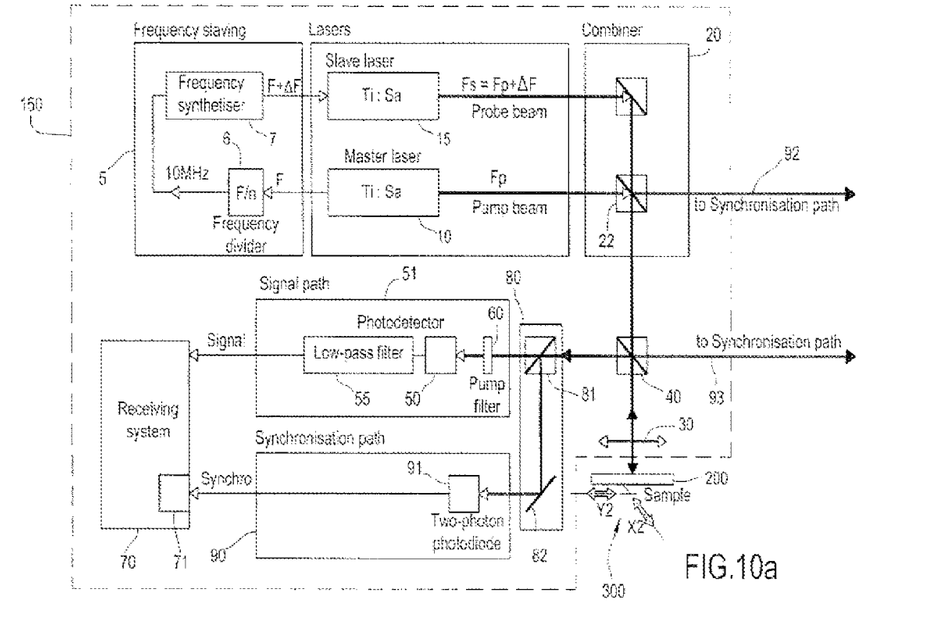
Figure 10B:
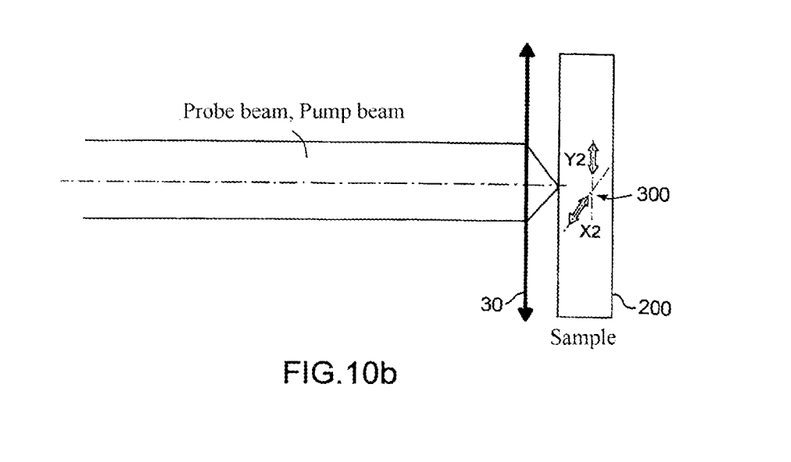

According to a further embodiment, described with reference to FIGS. 10a and 10b, the pump and probe beams are fixed and the scanning device 300 is thus a translation plate in the plane of the sample, on which plate the sample 200 is mounted.

The pump and probe beams shown in FIGS. 6 to 10 may be swapped around.

What is claimed is:

1. Optical heterodyne sampling device comprising two pulsed laser sources, which may have jitter and adapted to emit respectively a pump beam and a probe beam having respective pulse frequencies $F_s$ and $F_p$ where $F_s \neq F_p$, and a combining element for combining the pump and probe beams which are to be directed onto a sample, and further comprising a signal path, having a photodetection system for the sample reaction signal, and a receiving system for acquiring the detected photo signal which is connected to the signal path, wherein, $F_s$ and $F_p$ being substantially constant and the acquisition system comprising an acquisition triggering element, the device comprises a synchronisation path, which is connected to said triggering element and has a measuring device for measuring the beat frequency $|F_s - F_p|$ which is adapted to generate a synchronisation signal consisting of pulses for each time the pump and probe beam pulses coincide.

2. Device according to claim 1, wherein the measuring device comprises a two-photon photodiode.

3. Device according to claim 1, wherein it comprises a coupling device for coupling one laser source to the other.

4. Device according to claim 1, wherein the coupling device comprises a frequency divider which is disposed at the output of one laser source and a frequency synthesiser which is connected to said divider and to the other laser source.

5. Device according to claim 1, wherein the photodetection system is a photodetector or a row of photodetectors or a grid of photodetectors.

6. Device according to claim 1, wherein the laser sources have different wavelengths.

7. Device according to claim 1, wherein the pulse frequencies $F_s$ and $F_p$ are between 1 kHz and 10 GHz.

8. Device according to claim 1, wherein the pulse frequencies $F_s$ and $F_p$ are between 1 kHz and 100 MHz.

9. Device according to claim 1, wherein the synchronisation path comprising the measuring device for measuring $|F_s-F_p|$ is disposed in the path of the sample reaction signal.

10. Device according to claim 9, wherein it comprises a sample reaction signal separator, in two paths, the signal channel being disposed on one path and the synchronisation path on the other path.

11. Device according to claim 1, wherein the synchronisation channel is disposed in the path of the pump and probe beams which are to be directed onto the sample.

12. Device according to claim 1, wherein it comprises, disposed at the input of the photodetection system, a filter for the pump beam coming from the sample.

13. Device according to claim 1, wherein it comprises a low-pass filter disposed at the output of the reaction signal photodetection system.

14. Device according to claim 1, wherein the beat frequency $|F_s-F_p|$ is between 1 Hz and 100 kHz.

15. Device according to claim 1, wherein the laser sources are adapted to emit pulses having a duration of between 10 fs and 10 picoseconds.

16. Device according to claim 1, wherein the temporal resolution is approximately equal to one picosecond.

17. Device according to claim 1, wherein it comprises a scanning device for scanning the pump beam and/or the probe beam onto the sample.

18. Device according to claim 17, wherein the scanning device comprises two lenses and a displacement element for displacing the beam or beams.

19. Device according to claim 18, wherein the displacement element is a translation plate of a lens or comprises two galvanometric mirrors which can pivot around two respective perpendicular axes.

20. Device according to claim 17, wherein the scanning device can displace the pump beam and the probe beam, and in that the combiner comprises said scanning device.

21. Device according to claim 17, wherein the scanning device can displace the pump beam or the probe beam and is disposed downstream from the combiner.

22. Device according to claim 17, wherein the scanning device may comprise a translation plate for translating the sample.

23. Method for optical heterodyne sampling, using a device comprising two laser sources, which may have jitter and adapted to emit respectively a pump pulse beam and a probe pulse beam having respective pulse frequencies $F_s$ and $F_p$ where $F_s \neq F_p$, including a step of combining the pump and probe beams, a step of directing the combined pump and probe beams onto a sample, a step of photodetecting the sample reaction, and a step of acquiring the detected photo-signal, wherein, $F_s$ and $F_p$ being substantially constant, the method further includes a step of measuring the beat frequency $|F_s-F_p|$ in order to isolate an instant of coincidence between the pump and probe pulses, and in that the acquiring step is triggered as a function of the instant of coincidence.

24. Method according to claim 23, wherein it further comprises a step of coupling one laser source to the other.

25. Method according to claim 23, wherein the beat frequency $|F_s-F_p|$ is substantially equal to $\tau F_s F_p$, where $\tau$ is the duration of the probe beam pulses.

26. Method according to claim 23, wherein the sample reaction is obtained by reflection or transmission of the pump and probe beams.

27. Method according to claim 23, wherein it comprises a step of scanning the pump and/or probe beams onto the sample.

28. Method according to claim 23, wherein the pump and probe beams are superimposed.

29. Method according to claim 23, wherein the sample is a material in thin layers, an integrated circuit, a semiconductor, a biological cell or a chemical reagent.

30. Method according to claim 23, wherein the sampling has a temporal resolution of the order of a picosecond.

31. Method according to claim 23, wherein the laser sources can emit pulses having a duration of approximately 100 femtoseconds.

32. Method according to claim 23, wherein the beat frequency $|F_s-F_p|$ is between 10 Hz and 100 kHz.

33. Method according to claim 23, wherein the pulse frequencies $F_s$ and $F_p$ are between 0.1 MHz and 100 MHz.

* * * * *